Aug. 19, 1975 TAKESHI YOICHI YONEMOTO Plant Pat. 3,767
CARNATION PLANT
Filed Aug. 12, 1974
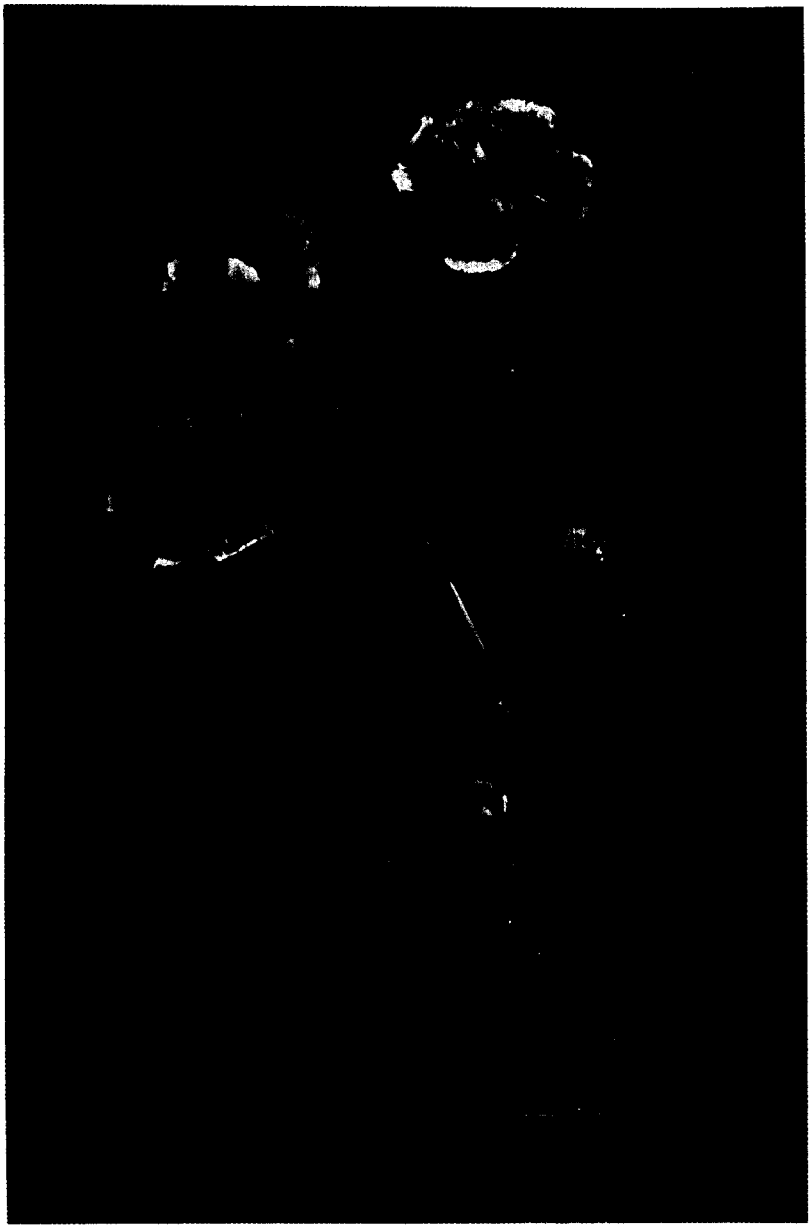
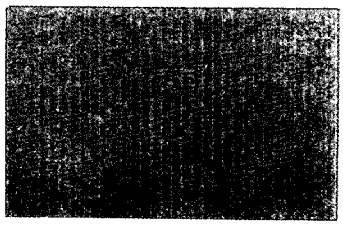

United States Patent

Plant Pat. 3,767

Patented Aug. 19, 1975

3,767

CARNATION PLANT

Takeshi Yoichi Yonemoto, 1328 Henderson Ave., Santa Clara, Calif. 95051

Filed Aug. 12, 1974, Ser. No. 497,127

Int. Cl. A01h 5/00

U.S. Cl. PH.—70

ABSTRACT OF THE DISCLOSURE

A new variety of carnation plant originated as a sport of Exquisite Select (unpatented) and distinguished by the deep purple and white coloration of its miniature size flowers, the flower petals having a solid purple body and a white marginal fringe.

*Background of the New Plant*

My new variety of carnation plant was discovered by me in 1970 among a group of plants of the Exquisite Select variety in my greenhouse at Santa Clara, Calif., and was noted because of its distinctive and lovely purple flowers, the outer petals of which have a narrow edging of white.

This sport was propagated by me, by means of cuttings, through several generations at Santa Clara, Calif., to test its stability and growth characteristics, and was found to have a vigorous growth habit with a profuse and continuous production of miniature blossoms borne in clusters on strong straight stems.

Continued propagation of this new carnation plant, by cuttings on greenhouse benches, has shown that the novel form and coloring of its blossoms holds true from generation to generation and appears to be firmly fixed. Propagation on a commercial scale is now being done at Santa Clara, Calif.

*Description of the Drawing*

This new variety of carnation plant is illustrated by the accompanying drawing which shows specimens of the flowers in full color, the color being reproduced as nearly true as it is reasonably possible to accomplish by conventional photographic procedures, the true color being shown by the color swatch affixed to the drawing below the subject image.

*Description of the New Plant*

The following is a description of this new variety of carnation plant with color designations according to the R.H.S. Colour Chart published by The Royal Horticultural Society, of London, England, in collaboration with the British Colour Council.

THE PLANT

Origin: Sport.
Parentage: Exquisite Select (unpatented).
Classification:
  Botanic—*Dianthus caryophyllus.*
  Commercial—Greenhouse variety for cut flowers.
Form: Bush.
Height: 2 to 3 feet.

Growth: Vigorous, upright and strong.
Growth Rate: Four months to blooming.
Foliage: Average abundance with 9 leaves per stem.
  Texture: Smooth.

THE BUD

Size: Small. Diameter—about ⅜ inch. Length—¾ inch.
Form: Long ovoid and pointed with white tip.
Sepals: Upright, generally linear in shape, about 1 inch long, with an acute apex having a white tip and margin.
Aspect: Smooth.
Opening Rate: Six days.
Splitting: None.

THE FLOWER

Blooming Habit: Perennial and profuse.
Size: Miniature. Diameter—1½ inches. Depth—¾ inch.
Borne: In clusters.
Shape: High centered cup.
Petalage:
  Number: 27 to 28.
  Form: Rounded fan shaped with lightly serrated end margin.
  Color: Face side of petals—R.H.S. 74A with white edges at tips of some petals. Reverse side—Lighter shade of the top surface color.
  Texture: Soft.
  Appearance: Velvety.
Fragrance: Slight.
Lasting Quality: 2½ weeks as cut flowers.

REPRODUCTIVE ORGANS

Stamens:
  Anthers: About ⅛ inch long. 12 in number.
  Filaments: Emerge from base of ovary. Length—¾ inch. Color—Light Green.
  Pollen: Color—Yellow.
Pistils: Number—2. Length—½ inch.
  Stigmas: Color—Purple.
Ovaries:
  Shape—Oblong, or like an upright egg.
  Size—⅝ x ⅜ inch.
  Color—Green.

This plant differs from its parent, Exquisite Select, by a reversal of the flower petal coloring. The flower petals of the parent variety are of a flushed purple color which blends into a darker orchid-like color at the end margins, whereas this new variety has a darker petal body the color of which blends into a somewhat lighter coloring toward the petal end margins.

I claim:

1. A new and distinct variety of carnation plant, substantially as herein shown and described, characterized by the deep purple color and narrow white edging of the outer petals of its flowers, by the miniature size of the flowers, and by its profusely blooming perennial growth habit.

No references cited.

ROBERT E. BAGWILL, Primary Examiner